United States Patent [19]

Lanier et al.

[11] Patent Number: 4,620,530
[45] Date of Patent: Nov. 4, 1986

[54] HALO TRACTION BRACE

[75] Inventors: Willard E. Lanier, Houston, Tex.; Juan B. Paez, Spring Arbor, Mich.

[73] Assignee: Camp International, Inc., Jackson, Mich.

[21] Appl. No.: 708,738

[22] Filed: Mar. 6, 1985

[51] Int. Cl.$^4$ ............................ A61F 5/04; A61F 5/37
[52] U.S. Cl. ...................................... 128/75; 128/87 B; 128/84 R
[58] Field of Search ........... 128/76 R, 87 B, DIG. 23, 128/75, 84 R

[56] References Cited

U.S. PATENT DOCUMENTS

| | | | |
|---|---|---|---|
| 443,764 | 12/1890 | Hilliard | 128/78 |
| 1,803,556 | 5/1931 | Nugent | 128/D 23 |
| 3,359,976 | 12/1967 | Laval, Jr. | 128/75 |
| 3,669,102 | 6/1972 | Harris | 128/84 R |
| 3,776,224 | 12/1973 | McFarland | 128/75 |
| 3,957,040 | 5/1976 | Calabrese | 128/75 |
| 4,245,627 | 1/1981 | Mignard | 128/75 |
| 4,541,421 | 9/1985 | Iversen et al. | 128/87 B |

FOREIGN PATENT DOCUMENTS 3302078 7/1984 Fed. Rep. of Germany ........ 128/75

OTHER PUBLICATIONS

"Ace Cervical Traction Equipment including the new Trippi-Wells Tongs and Mark II Halo"-Ace Orthopedic Company, 1981, pp. 38-39.
"The Most Advanced Halo/Vest System Available"--Bremer Orthopedics, Inc., pp. 40-41, 1982.
"Twin Cities Lo-Profile Halo System"-Depuy, pp. 42-43, prior to 3/6/84, exact data unknown.
"Durr-Fillauer Halo System"-Durr-Fillauer Medical, Inc., pp. 44-46, 1981.
"New from Jerome Medical Systems Halo Traction'-'-Jerome Medical Systems, Inc., 1983, pp. 48-51.
"Pope Brace Ambulatory Halos"-All Orthopedic Appliances, p. 52, 10-1982.
"The PMT Halo System"-Progress Mankind Technology, pp. 53-54, 1984.

Primary Examiner—Edgar S. Burr
Assistant Examiner—Tonya Eckstine
Attorney, Agent, or Firm—Beaman & Beaman

[57] ABSTRACT

The invention pertains to a traction brace for the head and neck wherein a head engaging ring is supported upon a torso-mounted vest. The vest consists of lateral sections interconnected by central parting lines and fasteners, and the head engaging ring is mounted upon columns extending above the vest sections. The apparatus is characterized by the accessibility to the patient that is provided.

5 Claims, 7 Drawing Figures

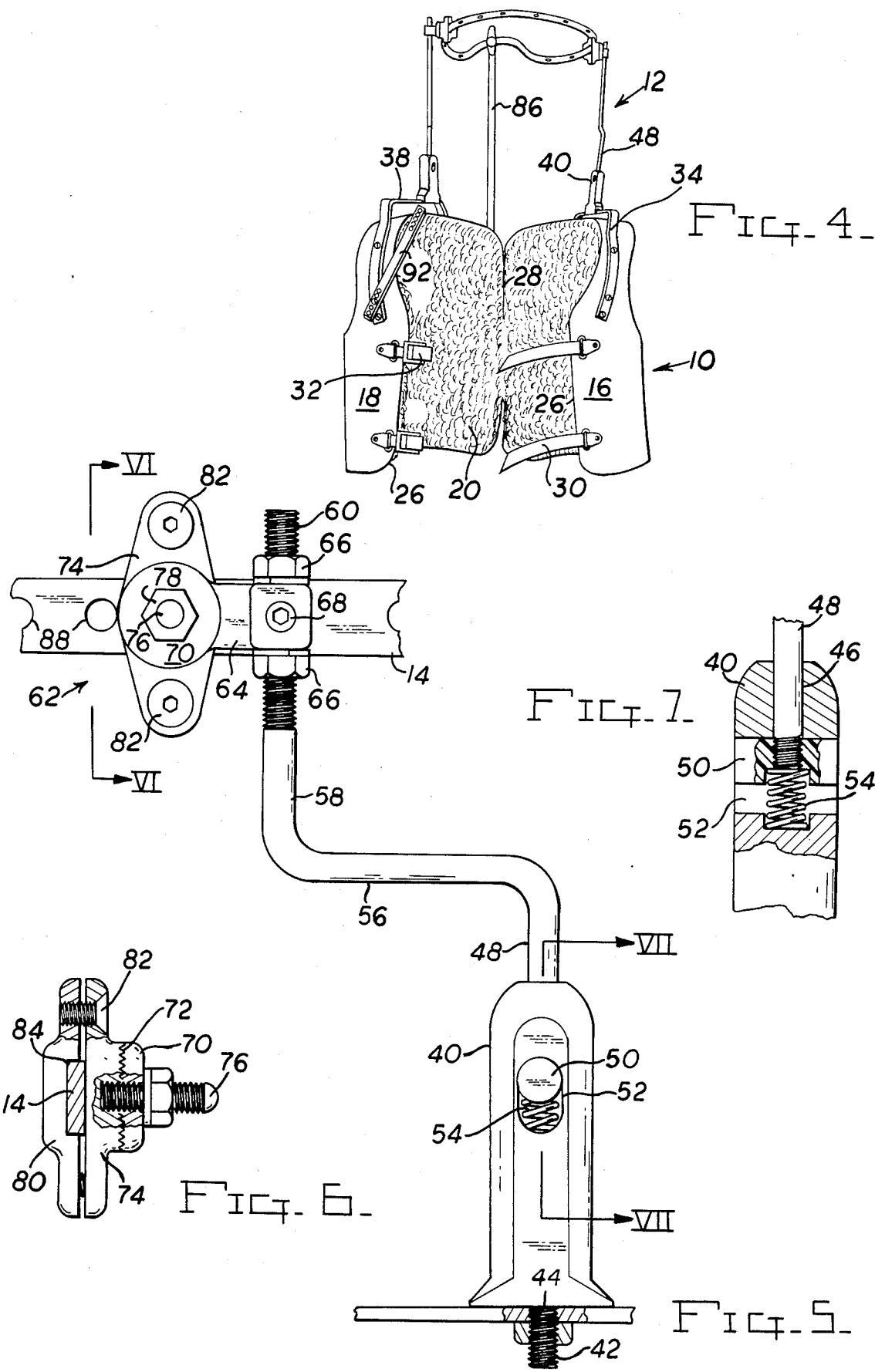

HALO TRACTION BRACE

BACKGROUND OF THE INVENTION

Ambulatory traction of the upper neck region can be provided by apparatus supported upon the torso having head engaging means for restricting head movement and maintaining the head and neck in traction. Such apparatus often includes a ring commonly termed a "halo" ring which surrounds the patient's skull and is attached thereto at various locations, usually by pins engaging the bone structure. With traction braces of this type, a torso encircling garment is usually used to support the halo ring columns, but prior garments have had the disadvantage of limiting access to the patient's chest area for medical monitoring and treatment purposes, as is often required with patients utilizing this type of appliance.

It is an object of the invention to provide an ambulatory traction brace which firmly supports the wearer's head and neck in a traction condition.

Another object of the invention is to provide an ambulatory traction brace for the head and neck wherein the brace is mounted upon a torso-encircling garment, and the garment is characterized by its ability to provide rapid access to the wearer, while being comfortable.

A further object of the invention is to provide an ambulatory traction brace which may be readily manufactured, is relatively comfortable, and may be easily donned and adjusted.

In the practice of the invention, the traction brace basically consists of a torso-encircling vest supporting columns upon which a head engaging halo ring is mounted. The vest consists of lateral sections each including an arm opening and front and rear parting lines centrally located at the wearer's chest and back. Releasable fastening straps mounted upon the vest sections hold the sections together upon the wearer's upper body region.

Rigid shoulder straps extend over the vest section arm openings, and lateral halo ring columns are mounted upon the shoulder straps and extend upwardly. Also, a rear column is mounted upon the rear sections for support of the rear portion of the halo ring.

The lateral ring columns include support structure permitting limited vertical movement, and the columns are biased in an upward direction by compression springs. The upper portion of the columns are attached to a halo ring by adjustable brackets permitting the desired angle of attachment to the halo ring, and head engaging means such as skull pins are mounted upon the halo ring to apply the traction forces to the head.

A brace bar extends across the front of the garment interconnecting the shoulder straps, while a similar rear brace bar extends across the rear of the garment interconnecting the rear portions of the shoulder straps, and in this manner, maximum rigidity is achieved, and as the rear column is attached to the rear brace bar, a firm rear column connection to the vest is assured.

Quick release fastening straps are mounted adjacent the front and rear parting edges of the vest sections, and the use of the straps permits the vest sections to be quickly opened. Also, a relatively low V-neckline of the vest renders the garment comfortable, and also aids in providing access to the wearer's chest region.

BRIEF DESCRIPTION OF THE DRAWINGS

The aforementioned objects and advantages of the invention will be appreciated from the following description and accompanying drawings wherein:

FIG. 4 is a front elevational view with the vest sections in the open condition, FIG. 5 is an enlarged, detail side view of a halo ring lateral column, FIG. 6 is an enlarged, partially sectioned view of a column and ring bracket as taken along Section VI—VI of FIG. 5, and FIG. 7 is an enlarged, detail, sectional view as taken through the ring column along Section VII—VII of FIG. 5.

DESCRIPTION OF THE PREFERRED EMBODIMENT

Figure 1:
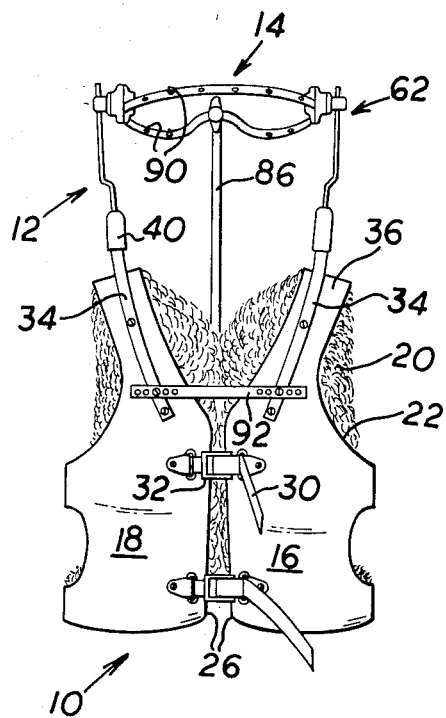
FIG. 1 is a front elevational view of a traction brace in accord with the invention, the vest sections being closed.

The basic components of a traction brace in accord with the inventive concepts include a vest 10 upon which lateral ring supporting columns 12 are mounted, and the columns support the head engaging ring 14. The ring 14 is commonly termed a "halo" ring with appliances of this type wherein traction forces are directly applied to the skull.

The vest 10 includes a left section 16 and a right section 18, and the vest sections are preferably formed of a relatively rigid synthetic plastic material and lined with a soft comfortable liner 20. The vest sections each include an arm opening 22 through which the wearer's arms extend, and the vest sections may include lateral cutouts 24 to reduce weight and improve air circulation.

Each of the vest sections includes a front vertically disposed parting line 26, and a rear vertical parting line 28, and quick acting fastening straps 30 and buckles 32. The buckles are infinitely adjustable along the length of the straps 30 and permit the front parting lines and rear parting lines, respectively, to be firmly drawn toward each other so that the vest snugly embraces the wearer's torso.

Rigid shoulder straps 34 are attached to the vest shoulder portions 36 extending over the arm openings 22. The shoulder straps are formed of metal, and at their uppermost region 38 are linear and provided with several holes to permit adjustable mounting of the lateral columns 12 thereon.

The lateral colums 12 include pedestals 40 engaging the upper surface of the shoulder strap portions 38, and a downwardly extending threaded stud 42 fixed to the pedestal extends through a shoulder strap hole 44, and a nut threaded thereon rigidly fixes the pedestal at the desired location upon the shoulder strap.

The pedestals 40 each include a vertical bore 46 receiving the column post 48 in a slidable manner, and the lower end of the post threadedly receives the nylon T-head 50. The head 50 is of an elongated, cylindrical configuration and is received within the oblong slot 52 defined in the pedestal. A compression spring 54 located within the pedestal biases the head and post upwardly, and the post 48 may be moved downwardly against this biasing force.

The column posts each include an offset horizontally disposed portion 56, and an upper portion 58 threaded at its upper end 60.

The upper end 60 of the columns supports a ring bracket 62 which includes an arm 64 having a vertical bore through which the threaded end 60 extends. Lock nuts 66 located on each side of the arm 64 tighten the arm at the desired position upon the end 60, and a set screw 68 is used as a safety lock to rigidly affix the arm 64 to the associated column post.

As appreciated from FIGS. 5 and 6, the circular portion 70 of the arm 64 is serrated at 72 to permit a variable angular orientation of the serrated adapter 74 to the arm about the threaded stud 76 mounted in the adapter and extending through the arm portion 70. The complementary serrations on the adapter rigidly lock the angular relationship between the arm and adapter upon the tightening of the stud nut 78 which draws the serrations into mesh.

The adapter bridge 80 is affixed to the adapter 74 by screws 82 and the bridge includes rectangular recess 84 receiving the halo ring 14. Thus, by tightening of the screws 82 the bridge 80 is drawn toward the adapter clamping the ring within recess 84.

In the aforedescribed manner, the lateral columns 12 are fixed to the halo ring 14 in predetermined adjustment thereto wherein a rigid interconnection between the halo ring and columns exist.

The halo ring 14 is a continuous ring of a configuration as apparent from the drawings. As noted, the rear portion of the ring may be offset in an upward direction for attachment to the rear column 86. The ring includes a plurality of holes 88 circumferentially spaced thereon, and within selected holes 88 skull pins 90 are mounted. The skull pins 90 are of a known type adapted to directly engage the skull bone structure in the conventional manner. Thus, tension forces applied to the columns 12 are transferred to the ring and directly to the wearer's head and neck.

To increase the stability and rigidity of the assembly, a rigid chest bar 92 is attached to the shoulder straps 34 by screws, FIG. 1. Likewise, a rear back bar 94 is attached to the rear portion of the shoulder straps 34 and a plurality of holes defined in these bars permits the bars to be readily attached to the shoulder straps regardless of the separation of the vest section parting lines due to the bulk of the wearer.

Figure 2:
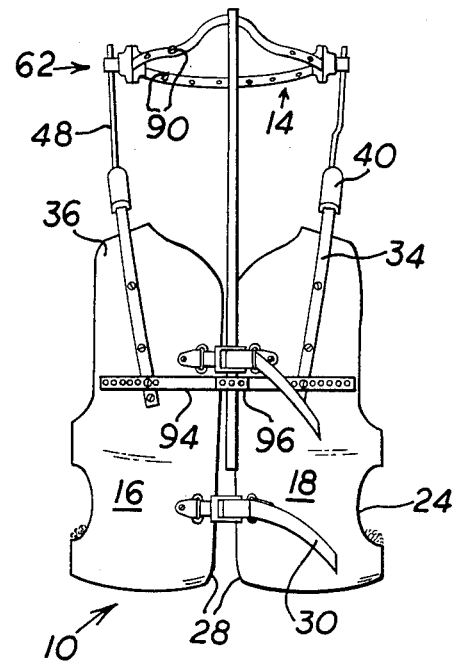
FIG. 2 is a rear elevational view of the traction brace, the vest sections being closed.
Figure 3:
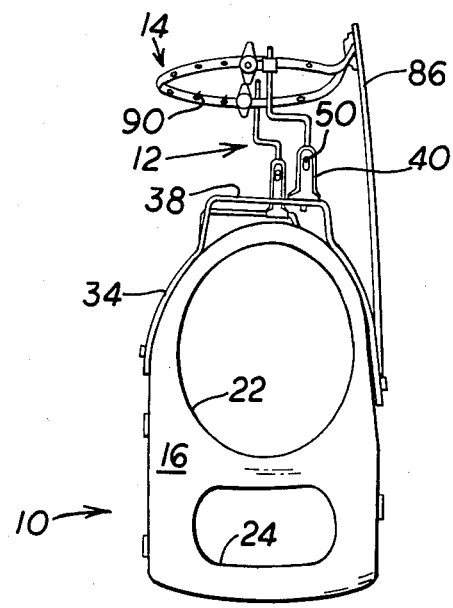
FIG. 3 is a left side, elevational view of the traction brace.

The back bar 94 also functions to support the rear column 86, FIG. 2, and the lower portion of the rear column is adjustably fixed to the bar 94 by bracket 96.

In use, the rear straps 30 and buckles 32 are preliminarily fastened and the vest is opened, as shown in FIG. 4 for donning by the patient. Thereupon, the vest is closed and the front straps 30 and buckles 32 fasten to snugly draw the vest sections about the wearer's torso. The front and rear bars 92 and 94 are then fixed in position, and the apparatus will be properly located upon the wearer for the desired location of the skull pins.

The springs 54 force the T-head 50 against the upper region of the pedestal slots 52, and as the columns are threaded into heads 50, limited rotational movement of the post with the T-head is possible, such as necessary to "open" the vest as shown in FIG. 4. If a sufficient downward force is exerted upon the posts, the posts will move downwardly compressing springs 54, and this "lost motion" aids in protecting the patient against harm. The rotational mounting of the post, and the presence of the offsets 56, does permit limited turning of the wearer's head without affecting the traction characteristics, and apparatus in accord with the invention is more comfortable than known apparatus of this type.

In the event of cardiac arrest or other serious medical problems, the front straps and buckles may be quickly opened, and the bar 92 removed permitting access to the wearer's chest, and this aspect of the invention is considered highly advantageous. Normally, the vest sections are lined with a relatively heavy cushioning fabric liner 20 to prevent chaffing and improve comfort, and apparatus in accord with the invention has been found to be more patient acceptable than known devices of this type.

It is appreciated that various modifications to the inventive concepts may be apparent to those skilled in the art without departing from the spirit and scope of the invention.

We claim:

1. A halo traction brace characterized by its accessibility to the wearer, comfort, stability and effectiveness comprising, in combination, a vest having two relatively rigid torso encircling lateral sections each having front, back and side portions, arm openings formed within said side portions, shoulder portions interconnecting said front and back portions of each vest section, each of said sections including a vertical front edge, said front edges forming a vertical front parting line centrally dividing said two sections at the front, each of said sections including a vertical back edge, said back edges forming a vertical back parting line centrally dividing said two sections at the back, fasteners mounted on said sections interconnecting said front and back portions, respectively, by selectively interconnecting said sections at said parting lines wherein said front edges and said rear edges, respectively, are positioned and maintained in adjacent, opposed relationship to each other during normal brace use by said fasteners, a halo ring stabilizing column mounted upon each shoulder portion extending above said shoulder portions, a halo ring attached to said columns, skull engaging means mounted upon said ring directly engaging the wearer's skull means to permit ready access to the wearer's chest while continuously maintaining stability between the halo ring and said vest sections, said last mentioned means including all of said fasteners, said fasteners interconnecting said back portions permitting said vest sections to hinge about said back parting line upon said fasteners interconnecting said front portions being released and said front portions being separated to provide access to the wearer's chest, and column adjustment means formed on said columns permitting said vest front portions to be separated while maintaining stability between said halo ring and said vest sections.

2. In a traction brace as in claim 1, rigid shoulder straps affixed to said vest extending over said shoulder portions, said columns being mounted upon said shoulder straps.

3. In a traction brace as in claim 1, spring means associated with said columns biasing said columns toward said halo ring in a vertical upward direction.

4. In a traction brace as in claim 3, said columns comprising elongated posts having an upper end portion and a lower end portion, said column adjustment means including portions of a common post being offset with respect to each other, said lower end portions being rotatably mounted upon said vest and said upper end portions being rotatable attached to said halo ring.

5. In a traction brace as in claim 4, a rear column having a lower end mounted upon said vest back portions and an upper portion attached to said halo ring.

* * * * *